United States Patent [19]

Kula et al.

[11] Patent Number: 5,330,905

[45] Date of Patent: Jul. 19, 1994

[54] METHOD FOR ISOLATING AN ENZYME FROM A FERMENTATION BROTH

[75] Inventors: Maria-Regina Kula, Niederzier-Hambach; Martin-Roger Grote, Lunen, both of Fed. Rep. of Germany

[73] Assignee: Forschungzentrum Juelich GmbH, Juelich, Fed. Rep. of Germany

[21] Appl. No.: 750,305

[22] Filed: Aug. 27, 1991

[30] Foreign Application Priority Data

Aug. 29, 1990 [DE] Fed. Rep. of Germany ....... 4027290

[51] Int. Cl.⁵ .......................... C12N 9/00; C12N 9/28; C12N 9/32; C12N 9/50
[52] U.S. Cl. ................................. 435/183; 435/202; 435/204; 435/219; 435/177; 435/180
[58] Field of Search ............... 435/183, 202, 204, 219, 435/177, 180

[56] References Cited

U.S. PATENT DOCUMENTS

| | | | |
|---|---|---|---|
| 3,943,072 | 3/1976 | Thomson et al. | 252/455 |
| 4,318,990 | 3/1982 | Thomson et al. | 435/219 |
| 4,690,892 | 9/1987 | Ananthapadmanabhan et al. | 435/183 |

OTHER PUBLICATIONS

Trevan, M. D. *Immobilized Enzymes* 1980, pp 68–71, John Wiley & Sons Ltd.
Shirai, Y. et al., Continuous production of monoclonal antibody with immobilized hybridoma cells in an expounded beci fermenter, Appli Microbiol Biotechnol 1987 26: pp.495–499.

*Primary Examiner*—David M. Naff
*Assistant Examiner*—Michael V. Meller
*Attorney, Agent, or Firm*—Foley & Lardner

[57] ABSTRACT

To obtain enzymes from an enzyme-containing suspension, such as fermentation broth, the suspension is placed, together with particulate material capable of binding enzyme, such as ion exchange resin, in a vertical container. An ascending stream of inert gas, such as dry nitrogen, is passed through the resulting composition at a rate sufficient for fluidization. The resulting composition is mixed and evaporated until an adequate amount of enzyme is bound to the particulate material. Concentration of enzyme in the suspension is directly proportional to the amount of enzyme bound to particulate material. The residual suspension is forced out of the container by a pulse of compressed gas, and the bound enzyme is eluted. To speed up the process, the stream of gas and/or the composition are heated to enzyme-tolerated temperatures. The resulting composition can be further subjected to a washing step after removal of the residual suspension and prior to elution of the enzyme. The washing liquid can be passed through another fixed bed column containing particulate material capable of binding enzyme. Elution of the enzyme can be carried out as a stepwise process.

20 Claims, 9 Drawing Sheets equilibrated column injection of the fermentation broth

Enzyme attachment

Elution of the attached enzyme

METHOD FOR ISOLATING AN ENZYME FROM A FERMENTATION BROTH

BACKGROUND OF THE INVENTION

The invention relates to a method for isolating enzymes from an enzyme-containing suspension, especially from untreated fermentation broth.

Various procedures for isolating enzymes from fermentation broths have been disclosed. Normally, these entail the initial removal of biomass by centrifugation or filtration, and the subsequent concentration of the resulting supernatant by ultrafiltration. See, for example, E. Flaschel et al., Advances in Biochem. Engr. Biotechn. 26 (1983) 73–142.

The known isolation methods are characterized by the loss of a considerable proportion of enzyme as a result of the initial step of separating the enzyme from the biomass. Moreover, these methods involve two separation steps which require time and effort.

SUMMARY OF THE INVENTION

It is therefore an object of the present invention to provide a method of isolating enzymes wherein enzyme loss and the required technical effort are minimal.

In achieving these objects, there has been provided in accordance with one aspect of the present invention, a method for isolating enzymes comprising the steps of (a) mixing an enzyme-containing suspension with particulate material capable of binding enzyme; (b) fluidizing the composition resulting from step (a) by passing an ascending stream of inert gas through said composition at a suitable rate to effectively mix the contents of said composition in said container; (c) evaporating said composition by passing said ascending stream of gas through said composition (d) removing said suspension from said composition; and (e) recovering bound enzyme by elution.

In accordance with another aspect of the present invention, a method has been provided wherein the ascending stream of gas is heated.

In accordance with yet another aspect of the present invention, a method has been provided which further comprises the step of heating the composition to enhance binding of enzyme to particulate material.

In accordance with a further aspect of the present invention, a method has been provided wherein the heating step is accomplished by applying an external heat source to the vertical container containing said composition.

In accordance with yet a further aspect of the present invention, a method has been provided wherein the suspension is comprised of an enzyme-containing fermentation broth.

In accordance with another aspect of the present invention, a method is provided wherein the steps are carried out in a vertical container.

In accordance with yet another aspect of the present invention, a method has been provided wherein the vertical container is a column.

In accordance with one aspect of the present invention, a method has been provided wherein the suspension is aqueous.

In accordance with a further aspect of the present invention, a method has been provided wherein the gas is dry nitrogen.

In accordance with yet a further aspect of the present invention, a method has been provided wherein the stream of gas is heated to enzyme-tolerable temperatures in order to effect evaporation.

In accordance with another aspect of the present invention, a method has been provided wherein said stream of gas and said composition are heated to enzyme-tolerable temperatures.

In accordance with yet another aspect of the present invention, a method has been provided wherein the particulate material is an ion exchange resin and wherein the resin is adjusted to a pH at which the enzyme is stable, the pH differing by at least one pH unit from the isoelectric point of the enzyme.

In accordance with a further aspect of the present invention, a method has been provided wherein the particulate material has a particle size ranging from 50 to 1000 $\mu$m.

In accordance with yet a further aspect of the present invention, a method has been provided wherein the particulate material has a particle size of about 100 $\mu$m.

In accordance with another aspect of the present invention, a method has been provided wherein the stream of gas is passed through the container until the enzyme loading of the particulate material is the optimum determined by the enzyme stability, the concentration-dependent proportion attached (ratio of the amount of enzyme attached to the adsorbent to the enzyme concentration in the liquid) and the attachment-reducing screening of charges by the load.

In accordance with yet another aspect of the present invention, a method has been provided wherein the suspension is removed from the container by a pulse of compressed gas.

In accordance with yet a further aspect of the present invention, a method has been provided further comprising the step of washing the composition after removing the suspension and prior to eluting the enzyme.

In accordance with another aspect of the present invention, a method has been provided wherein the suspension is added to the container in aliquots and evaporation the resulting composition is performed after the addition of each aliquot.

In accordance with yet another aspect of the present invention, a method has been provided wherein washing liquid is subsequently passed over a fixed bed column containing particulate material.

In accordance with yet a further aspect of the present invention, a method has been provided wherein the particulate material is ion exchange resin.

In accordance with a further aspect of the present invention, a method has been provided wherein the elution of the enzyme is carried out in a stepwise fashion.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
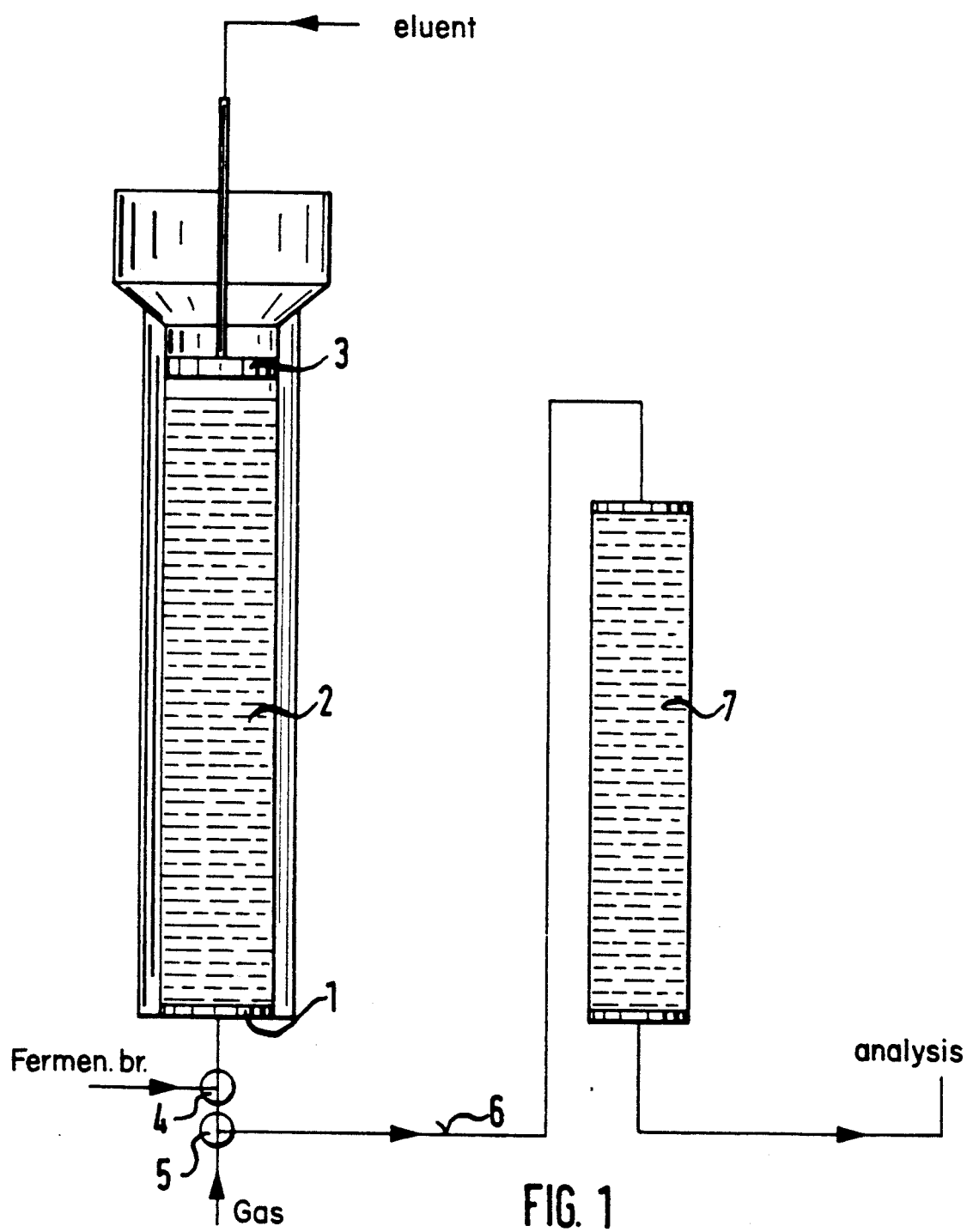
FIG. 1 is a schematic diagram illustrating how the method may be practiced in a laboratory setting.
Figure 2A:
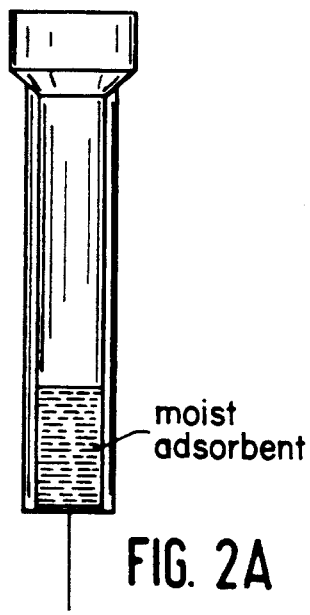
FIG. 2 illustrates the individual steps of the method according to the present invention.
Figure 2B:
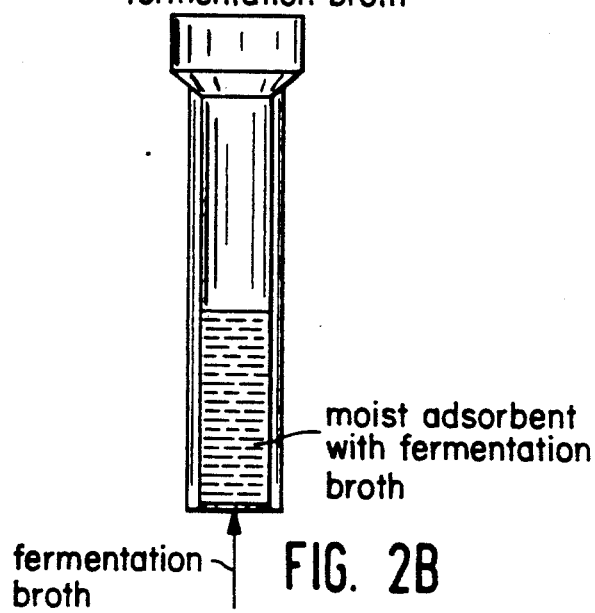
Figure 2C:
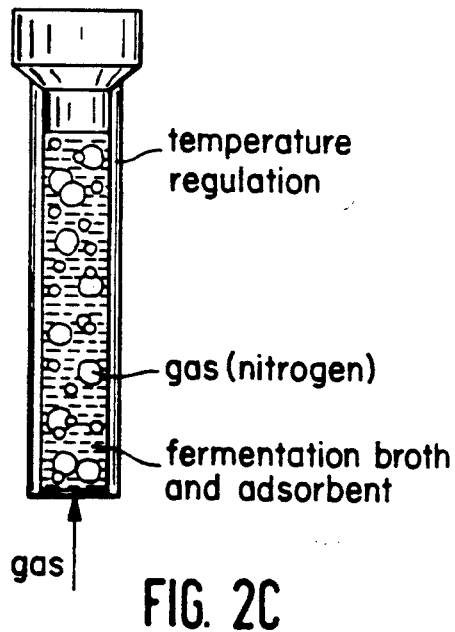
Figure 2D:
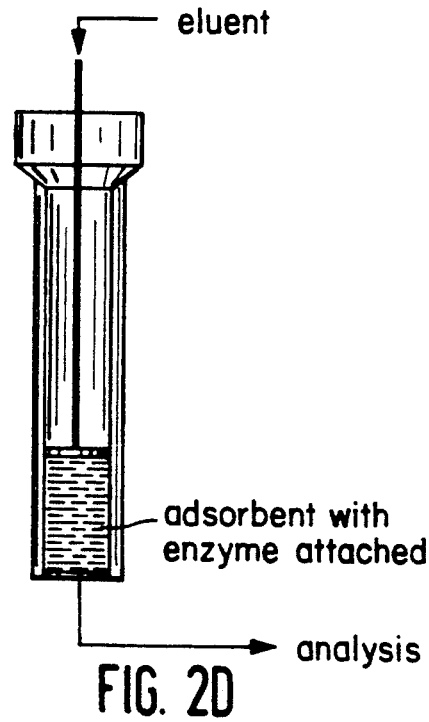

The method of the present invention does not require an initial removal of biomass. Instead, the biomass remains in the suspension and enzyme molecules are isolated by selective binding to a particulate material. Exemplary particulate materials which can be employed to bind enzyme molecules within the present invention include, but are not limited to, biospecific adsorbents used in affinity chromatography methods and hydrophobic support materials. Particularly preferred as particulate materials within the present invention are ion exchange materials which ensure that a substantial proportion of enzyme is isolated from the biomass-containing suspension.

In order to adequately mix the suspension containing enzyme molecules, biomass and particulate material in a vertical container such as a column, and, at the same time, concentrate the enzyme molecules, the suspension is fluidized (or "frothed") by passing an ascending stream of dry inert gas through the suspension until enzyme molecules have been concentrated by evaporation. The resulting concentration of enzyme molecules enhances their binding to the particulate material.

Throughout the steps of the isolation method, particular attention is paid to maintaining the temperature of the suspension at levels that will prevent substantial loss of enzyme activity due to heat inactivation. In addition, care is taken to maintain the enzyme concentration at an optimum level for binding to the particulate material. See FIG. 3 which illustrates the concentration-dependent binding equilibrium of free versus bound enzyme.

The amount of particulate material required for effective enzyme binding is dependent on the volume of the suspension to be processed, the binding affinity and capacity of the particulate material and the stability of the enzyme. While particulate material within the present invention is generally granular in nature, the particle size and shape of such material are not critical. As particle size increases there is a concomitant reduction in binding capacity. Granules with a particle size ranging from 40 to 150 μm have been effectively employed in the present invention. Exemplary of useful porous materials are open-pore sintered glass beads coated with a material which will bind enzyme molecules.

Generally, a minimal amount of particulate material is added to the suspension under the provision that the binding capacity of the material is sufficient so that the desired amount of enzyme is isolated from the suspension. If the binding affinity of the granules is low, causing the enzyme concentration in the residual suspension to remain high, evaporation should be continued for as long as possible before the residual suspension is removed from the column. Ratios of residual liquid to particulate material achievable by evaporation include ratios ranging as low as 0.08 ml/g.

When adding additional enzyme-containing fermentation broth to a suspension containing equilibrated granules, it is expedient to maintain a minimum ratio of total suspension to granules, e.g., 0.3 ml/g, which allows adequate mixing of the components with the aid of the ascending stream of gas. Maintaining an optimal ratio of total suspension to granules alleviates the need for initial mechanical stirring of the mixture.

Rather than increase the proportion of total suspension to granules in the column, in a preferred embodiment, aliquots of enzyme-containing fermentation broth are added periodically to the granule-containing column and intermediate evaporation is carried out in order to limit the height of the column. When broth is added periodically, the enzyme is bound to the granules for a minimum period of time which is advantageous when isolating relatively labile enzymes, particularly when evaporation is conducted at higher temperatures.

In order to adequately mix the enzyme-containing broth with the granules and effect evaporation of the resulting suspension in a column, an ascending stream of gas is passed through the suspension. Inert gases can be used according to the method of the present invention. In a preferred embodiment, nitrogen, is employed. In a particularly preferred embodiment, nitrogen in its dried form is employed to increase the rate of evaporation.

In order to achieve optimal mixing and rapid evaporation, the gas input and distribution are maximized. The bubble size of the gas stream depends, inter alia, on the viscosity of the suspension. In a preferred embodiment, bubble sizes ranging from about 0.2 to 1 cm are employed.

The particulate material/enzyme complex is separated from the residual suspension in order to isolate the enzyme. In a preferred embodiment, the particulate material/enzyme complex is separated from the residual suspension by techniques such as acceleration using pressure gradients. In another preferred embodiment, the biomass-containing residual suspension is separated from the particulate material/enzyme complex by expulsion using compressed gas. If separated from the residual suspension in this manner, the particulate material/enzyme complex can be washed and then treated with an eluent. The enzymes are eluted from the particulate material using stepwise elution when more than one enzyme is present, to fractionate the enzymes.

On a laboratory scale, the method according to the present invention can be carried out in an arrangement as illustrated in FIG. 1. In such an arrangement, a heatable column (#2) is equipped with a perforated plate (#1) which is closed by a movable plunger (#3) suitable for equally distributing the supply of eluent. Components of the suspension, particularly the fermentation broth, can be injected at an inlet (#4) beneath the column (#2), and gas is fed into the column via another inlet (#5). It would, of course, also be possible for the suspension to be fed into the column at another location.

The discharge from the column (#2) can be loaded via a connecting line (#6) onto a fixed bed column (#7) suitable for fractional elution. Due to the low biomass content, the suspension does not cause blockage of the column. In a preferred embodiment, the column (#2) has a widening at the upper end to slow down the stream of gas, and thereby avoid the ejection of packing with the emerging stream of gas. In a particularly preferred embodiment, the column (#2) has a conical widening at the upper end. The lower end can, where appropriate, have a conical taper.

FIG. 2 illustrates the essential phases of obtaining the enzymes: as shown in (a) the column (#2) is provided with moist equilibrated particulate material into which fermentation broth is fed, in particular by injection from below (b). The mixture of fermentation broth and particulate material is then fluidized or "frothed" by gas (c), and where appropriate heat is supplied via heated gas or a heating jacket, which results in good mixing and evaporation of the solvent (water). The supply and duration of heat depend in this stage of the process on (i) the stability of the enzyme(s) to be isolated, and (ii) the desired concentration of the liquid necessary to achieve maximal binding of enzyme to particulate material. Phase (c), a continual process, is employed when the enzyme is relatively stabile and exhibits only a moderate affinity for the particulate material, thereby necessitating maximal concentration of the enzyme in the suspension. Phase (c) is carried out until a quasi-viscous suspension results. The biomass-containing residual suspension is then expelled from the column by a build-up of pressure, which can be effected by redirecting the stream of gas from the bottom of the column to the top and subsequently releasing the pressure.

After this step is carried out, the moist particulate material is preferably washed briefly and then, as illustrated in (d), charged with eluent for fractional elution of the enzyme(s). In a preferred embodiment, the washing liquid is then directly loaded onto the fixed bed column (#7) (see FIG. 1) so that any enzyme present in the washing liquid can be recovered. Column (#7) also contains particulate material capable of binding enzyme.

The present invention is further described below by reference to the following, illustrative examples.

EXAMPLE 1

Fermentation broth composed of the following components and maintained at pH 7.0 was inoculated with *Bacillus licheniformis* in order to produce extracellular alkaline protease.

| "Synthetic Medium" ("SF Medium") | |
|---|---|
| glycerol (87%) | 22.971 g |
| ammonium sulfate | 6.000 g |
| potassium dihydrogen phosphate | 2.721 g |
| potassium hydroxide | 0.561 g |
| calcium chloride | 0.073 g |
| magnesium sulfate.7 $H_2O$ | 0.246 g |
| iron sulfate.7 $H_2O$ | 0.027 g |
| manganese sulfate.$H_2O$ | 0.008 g |
| trace elements | 0.010 l |
| double-distilled $H_2O$ | ad 1.000 l |
| nutrients | Σ = 26.000 g |

In an apparatus as illustrated in FIG. 1, wherein the height of the column (#2) was 300 mm and the internal diameter was 26 mm, 50 g of ion exchanger resin (Fractogel EMD $SO_3$-650 (C), supplied by Merck, Darmstadt) with a particle size ranging from 90 to 150 μm were equilibrated with 200 ml of buffer ($KH_2PO_4$/$Na_2HPO_4$ buffer; pH 5; 67 mM). After equilibrating the resin, the buffer was drained out of the column, and fermentation broth was injected into the bottom portion of the column via a syringe. A controlled stream of nitrogen was then introduced into the bottom portion of the column and passed upwards through the column in order to fluidize the resin and fermentation broth. "Fluidization" in this context refers to the mixing of a suspension containing resin and enzyme-containing fermentation broth caused by passing a stream of gas through such a suspension at a rate sufficient to effectively mix the suspension contents. The column was heated to 50° C. in order to cause evaporation of the broth and facilitate binding of enzyme to the resin. After about 15-60 minutes, the remaining fermentation broth was removed from the "fluidized bed adsorption column".

The remaining fermentation broth was removed by redirecting the stream of gas from the bottom part of the column to the previously sealed upper part of the column. Pressure (one bar) formed in the upper part of the column. The lower drain was then opened so that the broth was forced at high speed out of the resin and subsequently discarded. This step removed most of the unattached biomass from the particulate material. The moist Fractogel was then washed with 100 ml of water. The wash liquid was passed over the additional fixed bed column (#7) where the enzyme molecules desorbed in the washing step were "adsorbed" or immobilized again.

In order to elute the enzyme, column (#2) was reconfigured as a fixed bed column (FIG. 2d) by lowering the plunger as far as the level of the particulate material packing. Care was taken during this step to ensure that sufficient washing water remained between the particles to avoid air bubbles. The eluent was then added to the upper part of column (#2) and the discharge was passed through the additional fixed bed column (#7). The eluted enzyme (desorbate) was collected with a fraction collector for further analysis.

Various experiments were carried out as described below.

Fermentation broth containing protease was obtained from various fermentations (A and B). Fractogel was equilibrated to pH 5 with the $KH_2PO_4$/$Na_2HPO_4$ buffer before each experiment. In each case, 15 ml of fermentation broth was mixed with 50 g of Fractogel and distilled water was used as the washing liquid.

Enzyme elution was carried out by either a continuous (with "gradient") increase or by a stepwise increase in salt concentration and increase in the pH. Fractogel utilized in the experiments was regenerated with 0.5M sodium hydroxide solution.

In Experiment 1, enzyme was eluted with $Na_2HPO_4$/NaOH buffer adjusted to pH 11.0 containing 1M NaCl. Buffers with different salt concentrations were employed as eluents in Experiments 2 to 5. In Experiment 5, the washing liquid was passed through the additional fixed bed column which was packed with 50 g of Fractogel.

Individual parameters of the experiments and the concentration of protease in each of the experiments are listed in Table 1.

TABLE 1

| Experiment | Protease concentration | Type of desorption | Column temp. | Evaporation | Fermentation |
|---|---|---|---|---|---|
| 1 | 1571 PU/ml* | Gradient | 20° C. | 43.3% | A |
| 2 | 2554 PU/ml | Stepwise | 40° C. | 56.7% | B |
| 3 | 2524 PU/ml | Stepwise | 50° C. | 77.3% | B |
| 4 | 2282 PU/ml | Stepwise | 40° C. | 44.0% | B |
| 5 | 2589 PU/ml | Stepwise | 50° C. | 72.0% | B |

*348 PU/ml = 1 U/ml (Ansonunit, J. Gen. Physiol. 22 (1938) 79–89)

Table 2 reports the percentage of adsorbed and desorbed enzyme relative to the total amount of enzyme present in the fermentation broth before adsorption.

TABLE 2

| Experiment | Adsorbed amount of enzyme | Desorbed amount of enzyme |
|---|---|---|
| 1 | 84.5% | —* |
| 2 | 87% | 55.9% |
| 3 | 91.4% | 56.6% |
| 4 | 86.1% | 56.4% |
| 5 | 91.1% | 78.7% |

*Enzyme already completely desorbed in the washing step.

Figure 3:
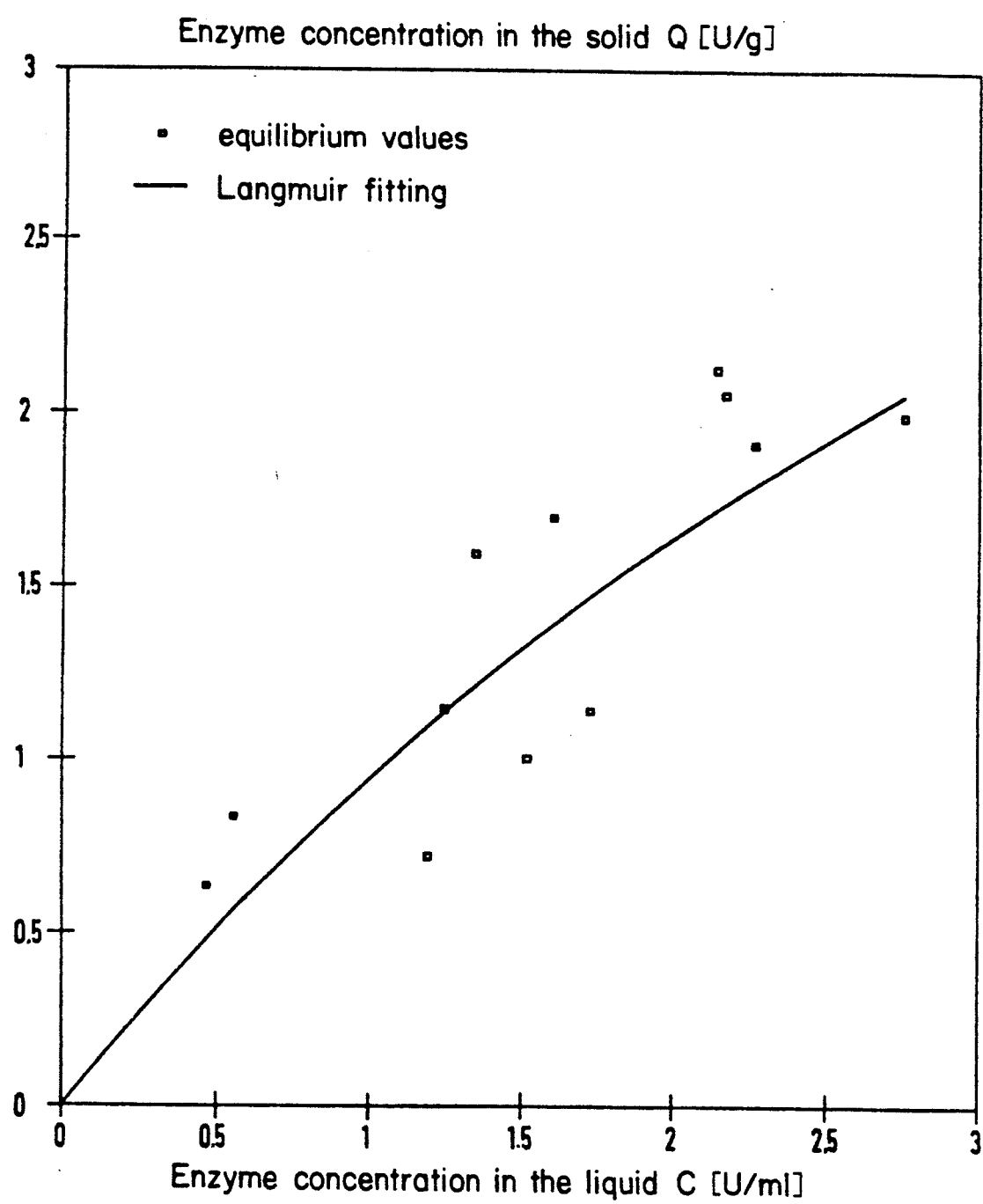
FIG. 3 illustrates equilibrium values of bound versus free enzyme.

Due to the increased viscosity of the suspension resulting when 15 ml of fermentation broth was added to 50 g of Fractogel, a maximum of about 75% of the fermentation broth could be evaporated. The maximum amount of enzyme bound to the particulate material under these condition was between 91 and 92%. The increase in the percentage of bound enzyme due to evaporation is illustrated in FIG. 3.

Figure 5:
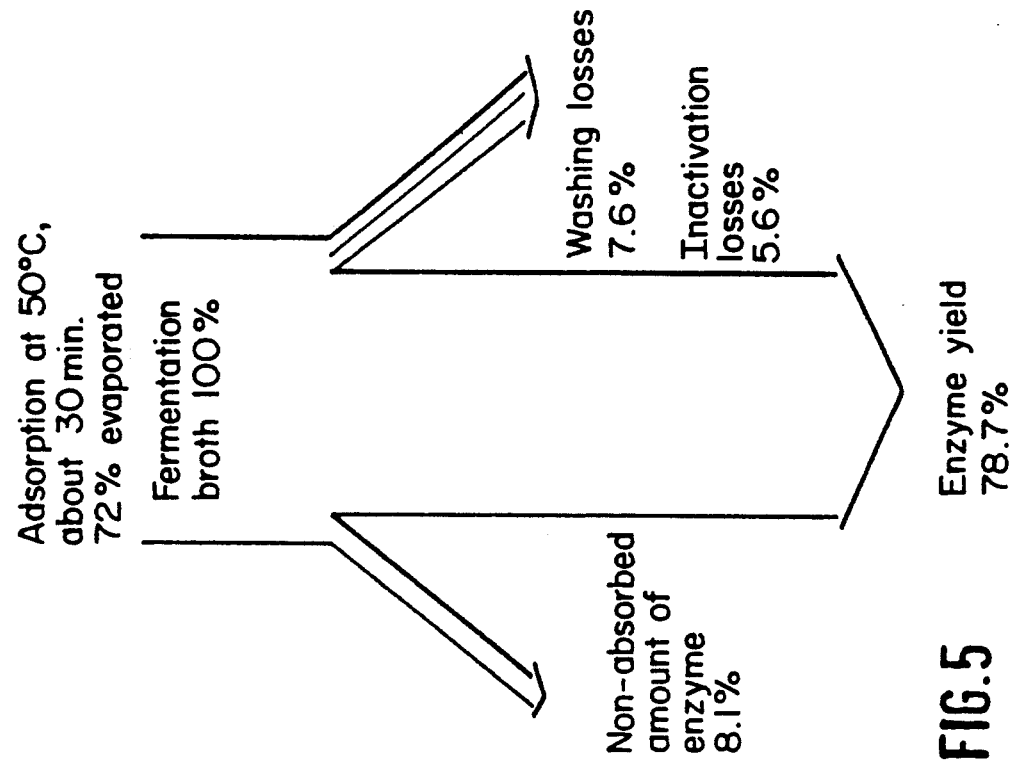
FIG. 5 illustrates the amount of enzyme (i) isolated, (ii) lost due to washing, lost due to heat inactivation, and (iv) remaining in the residual suspension when the method is carried out at 50° C. for about 30 minutes.
Figure 4:
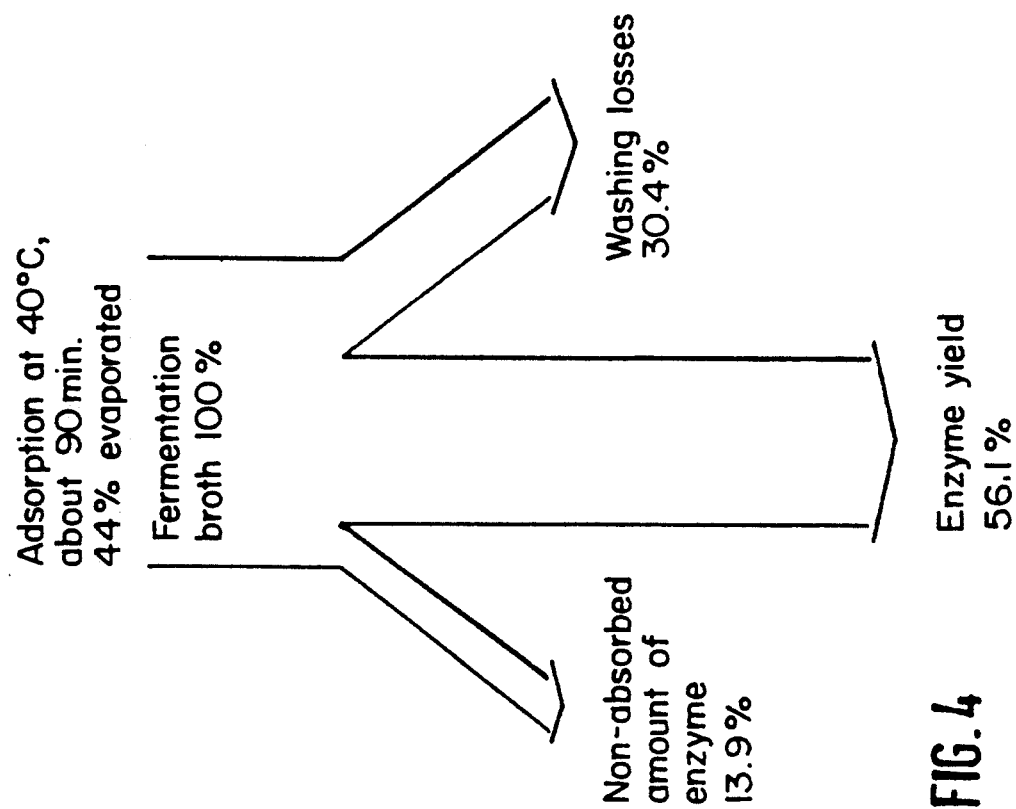
FIG. 4 illustrates the amount of enzyme (i) isolated, (ii) lost due to washing, lost due to heat inactivation, and (iv) remaining in the residual suspension when the method is carried out at 40° C. for about 90 minutes.

The loss of enzyme due to washing can be reduced by an additional fixed bed column. This principle was illustrated by comparing the balanced amount of enzyme in Experiment 4 (FIG. 4) with that of Experiment 5 where an additional column was employed (FIG. 5). The amount of protease present in the desorbate increased relative to the original amount of protease in the fermentation broth from 56.4% to 78.7%. These results are presented in Table 3.

TABLE 3

| Experiment | Fermentation broth used U | Fermentation broth used % | Non-adsorb. amount of enzyme used U | Non-adsorb. amount of enzyme used % | Washing losses U | Washing losses % | Thermal inactivation U | Thermal inactivation % | Desorbed amount of enzyme U | Desorbed amount of enzyme % |
|---|---|---|---|---|---|---|---|---|---|---|
| 4 | 94.4 | 100 | 13.7 | 13.9 | 29.9 | 30.4 | | | 55.5 | 56.4 |
| 5 | 111.6 | 100 | 9.0 | 8.1 | 8.5 | 7.6 | 6.3 | 5.6 | 87.8 | 78.7 |

| Experiment | Adsorption temperature °C. | Evaporation % | Adsorption time s | Additional adsorption column for the washing liquid |
|---|---|---|---|---|
| 4 | 40 | 44 | 5400 | not used |
| r | 50 | 72 | 1800 | used with 50 g of adsorbent (moist) |

Figure 7:
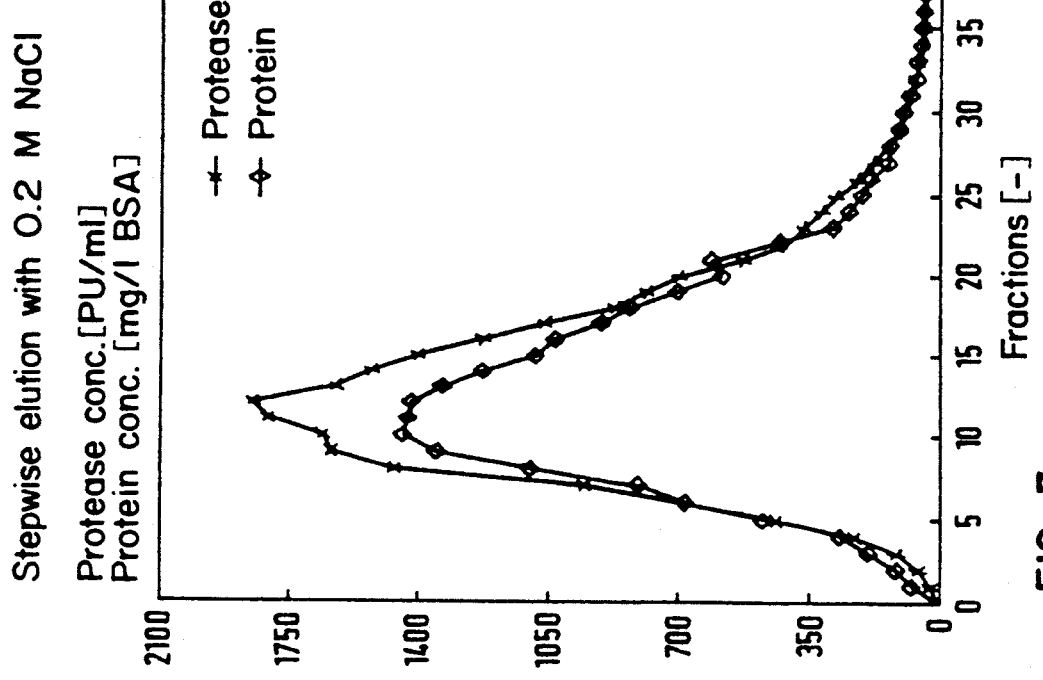
FIGS. 6 and 7 illustrate the results of experiments eluting protease.
Figure 6:
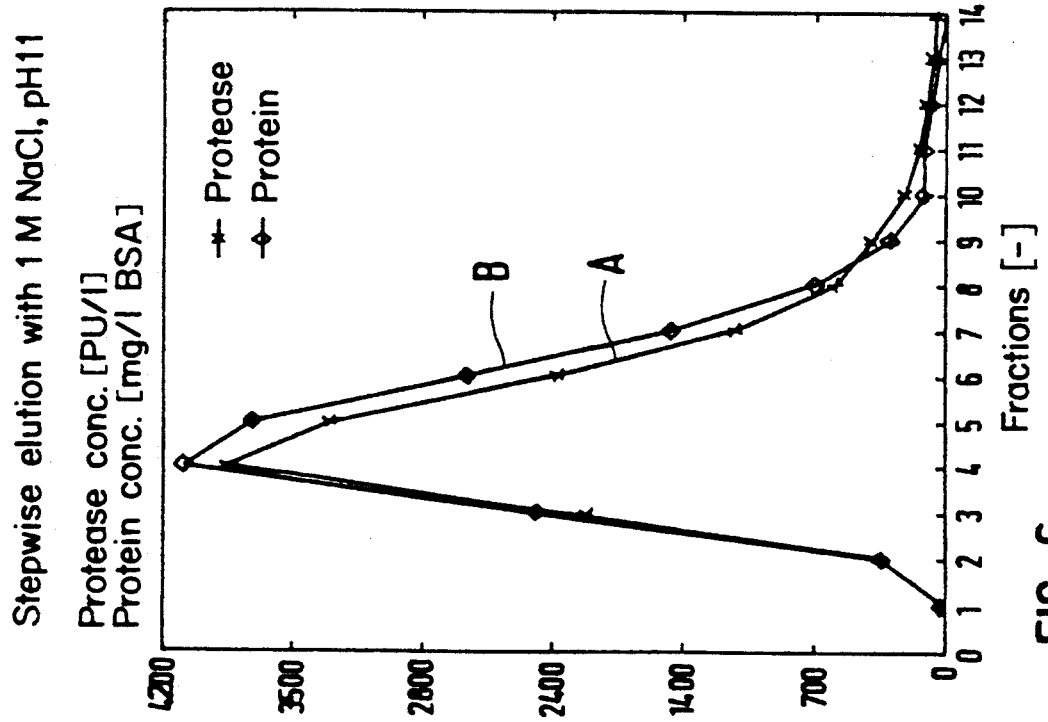

FIGS. 6 and 7 illustrate the results of two experiments to isolate protease according to the method of the present invention. FIG. 6 illustrates the elution profile of a protease derived from Bacillus licheniformis. Protease activity is depicted by plot (A). The protein content in the eluate is depicted by plot (B). Plots A and B have the same shape.

Figure 8:
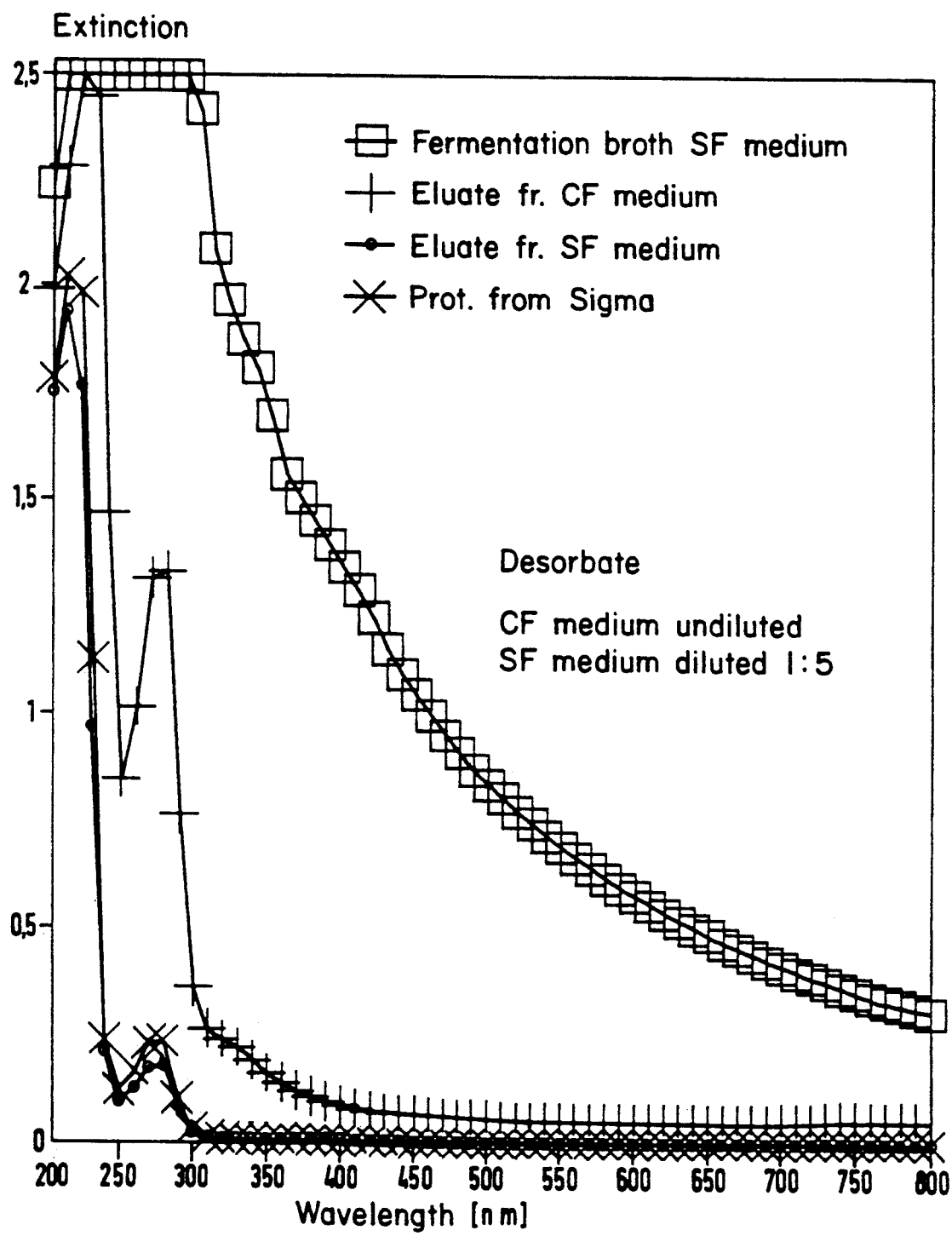
FIG. 8 illustrates the absorption spectra for eluted enzyme compared with fermentation broth and commercial protease.

FIG. 8 illustrates the absorption spectra for (i) fermentation broth, (ii) for enzyme obtained as eluate, and (iii) for a commercially available (Sigma) protease. While the absorption spectrum of the enzyme obtained according to the method of the present invention is identical to that of the commercially available protease, the fermentation broth produces a significantly different absorption spectrum. The fact that both the commercially available protease and the protease isolated according to the method of the present invention produce identical absorption spectra is evidence that the foreign protein content in the eluate is extremely low.

This result was confirmed by gel electrophoresis of the eluate and a solution of the purified enzyme. Both the eluate and the protease produced a band at=27,500 Dalton. No impurities were evident in either of the samples. Moreover, the specific activity of enzyme isolated according to the method of the present invention was 1 and ½ times greater than the activity of the commercially available protease.

EXAMPLE 2

Figure 9:
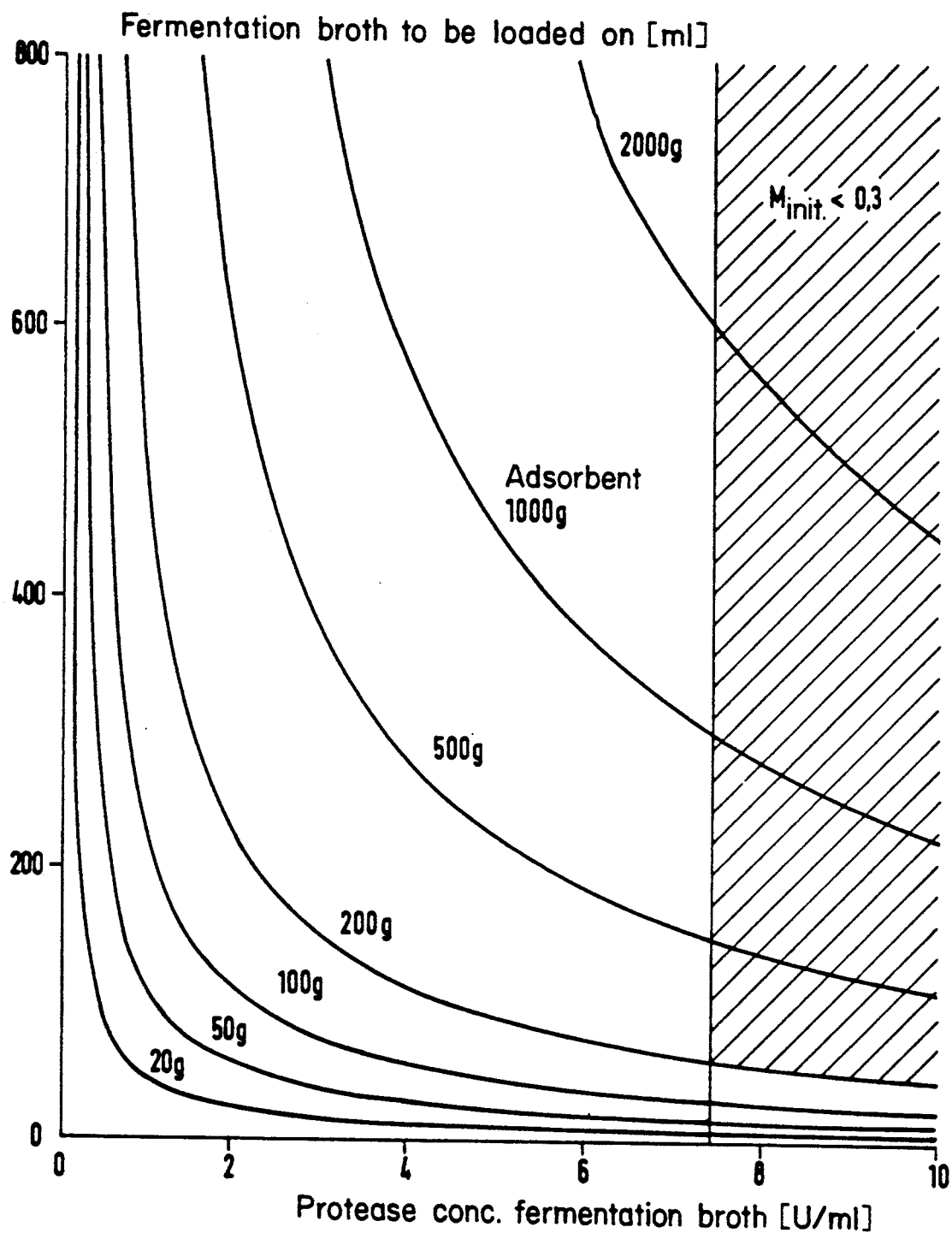
FIG. 9 illustrates the effect of packing a column with varying amounts of Fractogel for binding protease.

The optimal efficiency parameters of a column utilized according to the method of the present invention were calculated for binding protease to Fractogel (see FIG. 9). The parameters used in this calculation were based on results indicating that at least 2 U/g of enzyme can be bound to Fractogel with 2.6 U/ml of protease remaining in the residual suspension.

The calculations indicated that the ratio of fermentation broth to particulate material should be maintained at 0.3 ml/g in order to obtain maximum yield of enzyme and maximum binding of enzyme to particulate material. At lower ratios, it is more difficult to effect initial mixing of moist particulate material with injected suspension. Once the amount of enzyme is concentrated by evaporation according to the method of the present invention, a low ratio of residual suspension to granules should be maintained in order to minimize enzyme loss upon removal of the residual suspension. Minimum ratios of 0.08 ml/g have been achieved in practice. The ratios of broth to granules and of residual suspension to granules were included in the calculation.

FIG. 9 shows the amount of particulate material required for maximum yield of enzyme and maximum binding of enzyme to particulate material as a function of the volume of the fermentation broth and of its protease concentration. The shaded area indicates the region in which the initial ratio of the two is below 0.3 ml/g. At ratios below 0.3 ml/g, initial mixing of particulate material and fermentation broth was only possible with additional mechanical stirring.

When practicing the method of the present invention, the working volume of the column (#2) should be at least twice as large as the space occupied by the particulate material as there is a 100% increase in packing of the particulate material due to the addition of suspension and expansion caused by the ascending stream of gas. Greater column heights can be utilized. The amount of suspension necessary to achieve the calculated parameters can be added to the column in its entirety. Alternatively, the suspension can be added to the column in aliquots with intermediate evaporation if the column has insufficient capacity when fluidized with gas to handle the total amount of suspension.

EXAMPLE 3

Extracellular alkaline protease and α-amylase were produced according to the methodology of Example 1 in a fermentation broth, pH 7, containing the following components:

| "CF Medium" | |
|---|---|
| corn starch | 90.000 g |
| α-amylase | 0.100 g |
| sodium caseinate | 25.000 g |
| soybean flour | 19.000 g |
| corn steep liquor | 7.000 g |
| ammonium dihydrogen phosphate | 0.500 g |
| disodium hydrogen phosphate | 0.500 g |
| potassium dihydrogen phosphate | 0.200 g |
| iron sulfate.7 H$_2$O | 0.048 g |
| manganese sulfate.H$_2$O | 0.020 g |
| H$_2$O | ad 1.000 l |
| nutrients | Σ = 141.000 g |

This medium promotes the extracellular production by *Bacillus licheniformis* of α-amylase as well as alkaline protease. Separation of alkaline protease from the complex fermentation medium is impeded by the considerably higher nutrient content (5 times greater) of this medium relative to the Synthetic Medium of Example 1 and by the presence of the second extracellular enzyme.

Tables 4 and 5 present the results of experiments carried out with CF Medium.

TABLE 4

| Experiment | $C_{FB}$ [PU/l] | $C'_{FB}$ [PU/l] | Desorbed Amount of Enzyme [PU] | Yield [%] | Fermentation Broth Loaded on [ml] |
|---|---|---|---|---|---|
| 1 | 2631 | 1540 | 21030 | 39.3 | 20 |
| 2 | 2099 | 980 | 19341 | 61.4 | 15 |
| 3 | 2329 | 998 | 21255 | 60.3 | 15 |
| 4 | 2146 | 1036 | 22277 | 69.0 | 15 |
| 5 | 2578 | 1206 | 20840 | 53.9 | 15 |
| 6 | 2547 | 1499 | 25160 | 49.4 | 20 |
| 7 | 2004 | 1063 | 18569 | 61.8 | 15 |
| 8 | 2281 | 699 | 26891 | 78.6 | 15 |
| 9 | 2486 | 2180 | 22357 | 36.0 | 25 |
| 10 | 2354 | 1833 | 21286 | 45.2 | 20 |
| 11 | 1914 | 1967 | 19687 | 34.3 | 30 |
| 12 | 2826 | 2044 | 22838 | 27.1 | 30 |
| 13 | 1940 | 897 | 19827 | 68.2 | 15 |
| 14 | 2609 | 978 | 21117 | 54.0 | 15 |
| 15 | 1956 | 655 | 15791 | 53.8 | 15 |
| 16 | 2335 | 686 | 19583 | 55.9 | 15 |
| 17 | 2587 | 734 | 22858 | 58.9 | 15 |
| 18 | 2638 | 2607 | 28350 | 30.7 | 35 |
| 19 | 2947 | 565 | 15360 | 69.5 | 7.5 |
| 20 | 2524 | 350 | 13482 | 71.2 | 7.5 |
| 21 | 2631 | 2519 | 30476 | 33.1 | 35 |
| 22 | 2779 | 2330 | 23812 | 28.6 | 30 |
| 23 | 2914 | 2445 | 29293 | 22.3 | 45 |

$C_{FB}$: Enzyme concentration in the fermentation broth
$C'_{FB}$: Enzyme concentration in the residual suspension after adsorption and evaporation

TABLE 5

| Experiment | C [mS/cm] | C' [mS/cm] | pH [−] | pH' [−] | Evaporated Fermentation Broth [%] | Fermentation Broth Loaded on [ml] |
|---|---|---|---|---|---|---|
| 1 | 1.24 | 1.19 | 6.79 | 6.25 | 77 | 20 |
| 3 | 1.03 | 0.92 | 6.84 | 6.29 | 66 | 15 |
| 4 | 1.11 | 0.91 | 6.78 | 6.25 | 63 | 15 |
| 5 | 1.11 | 0.98 | 6.82 | 6.19 | 61 | 15 |
| 8 | 1.09 | 0.67 | 6.81 | 6.39 | 78 | 15 |
| 10 | 1.06 | 1.13 | 6.81 | 6.37 | 89 | 20 |
| 11 | 1.09 | 1.57 | 6.84 | 6.48 | 69 | 30 |
| 12 | 1.08 | 1.36 | 6.84 | 6.38 | 72 | 30 |
| 13 | 1.05 | 0.97 | 6.83 | 6.29 | 77 | 15 |
| 14 | 1.08 | 0.85 | 6.80 | 6.33 | 65 | 15 |
| 15 | 1.07 | 0.73 | 6.84 | 6.31 | * | 15 |
| 16 | 1.12 | 0.79 | 6.77 | 6.25 | 3 | 15 |
| 17 | 1.10 | 0.78 | 6.77 | 6.29 | 0 | 15 |
| 18 | 1.09 | 1.26 | 6.77 | 6.52 | 79 | 35 |
| 19 | *1.10 | 0.79 | 6.68 | 6.01 | 13 | 7.5 |
| 20 | 1.08 | 0.67 | 6.72 | 6.02 | 59 | 7.5 |
| 21 | 1.06 | 1.33 | 6.68 | 6.31 | 81 | 35 |
| 22 | 1.11 | 1.42 | 6.74 | 6.35 | 65 | 30 |
| 23 | 1.10 | 1.64 | 6.69 | 6.53 | 79 | 45 |

*In experiment 15, the fermentation broth was diluted with distilled water (dilution factor 1.44).
pH: pH value
C: Conductivity
': Relates to the fermentation broth after adsorption.

When using the methodology of Example 1, only 61% of the enzyme employed was desorbed (see Experiment 2). However, this value was increased to 78% by increasing the amount of Fractogel in the additional fixed bed column (FIG. 1, column 7) from 50 g to 130 g (see Experiment 8). This higher value (78%) is comparable with yields achieved in Example 1. The results demonstrate that the greater the amount of fermentation broth loaded on the column, the lower the yield achieved. This phenomenon may be due to the limited binding capacity of the adsorbent.

Figure 10:
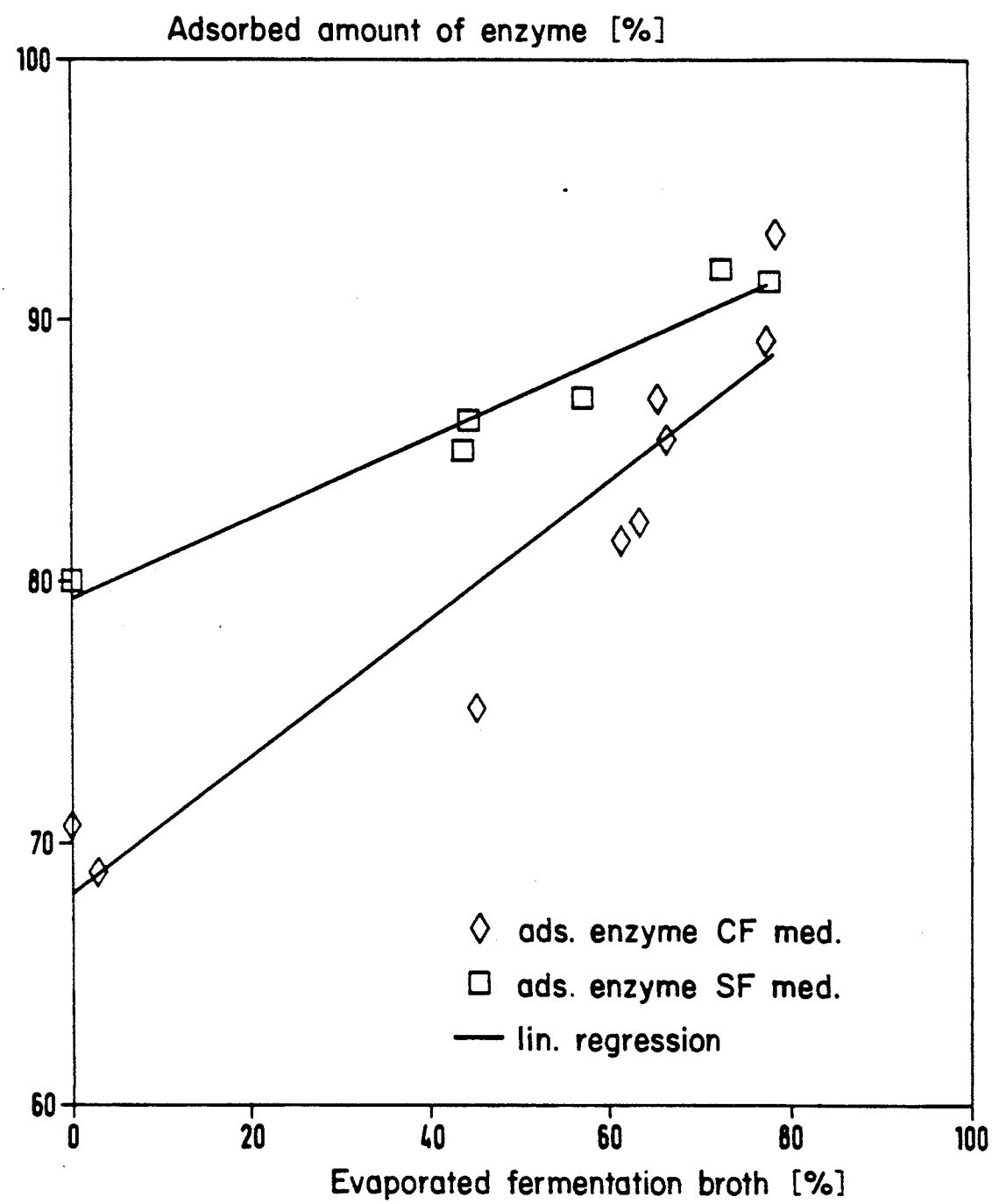
FIG. 10 illustrates the amount of bound enzyme as a function of the evaporated concentration of the suspension.

The effect of evaporating the fermentation broth is illustrated in FIG. 10. The amount of enzyme bound to the particulate material can be increased by evaporation from about 20% to about 90%. These results were achieved when 15 ml of fermentation broth was added to the column.

In FIG. 8, a qualitative comparison of enzyme isolation from SF Medium versus CF Medium according to the method of the present invention is illustrated. The two eluates exhibit identical plots which demonstrates that it is equally possible to achieve good selective isolation of protease from a complex fermentation medium.

EXAMPLE 4

In order to isolate extracellular α-amylase from CF fermentation broth as produced in the methodology of Example 3, Fractogel EMD (M) TMAE (supplied by Merck, Darmstadt), an anion exchange resin with a particle size of 45–90 μm was chosen as the particulate material. 50 g of Fractogel EMD (M) TMAE was packed into each of columns 2 and 7 (FIG. 1) and equilibrated with about 200 ml of buffer (tris-HCl buffer; pH 8.0; 50 mM). α-amylase was recovered in the first fractions of the washing liquid (distilled water) according to the methodology described in Example 1. While only impurities were eluted on desorption, this procedure resulted in efficient and qualitatively good isolation of α-amylase.

Figure 11:
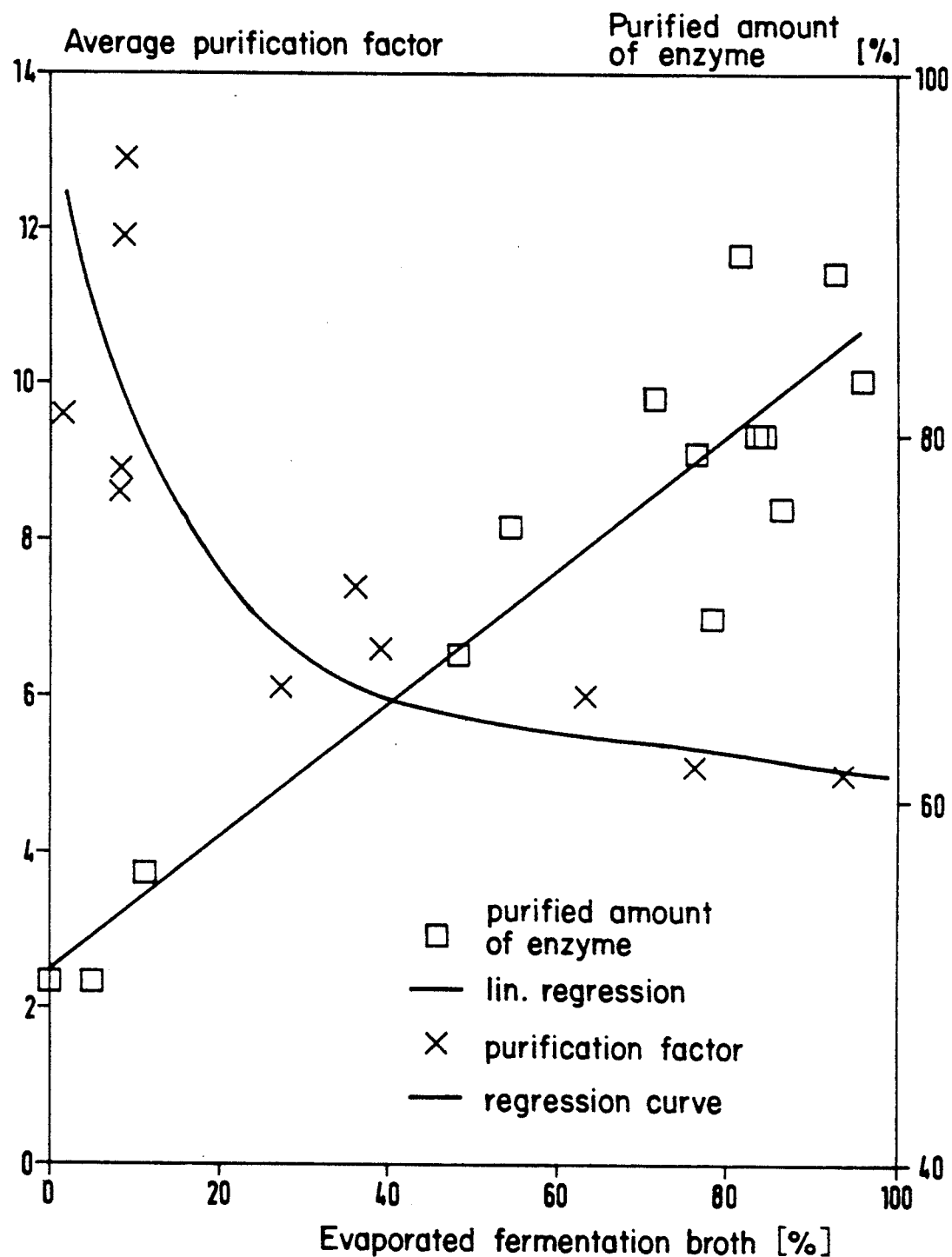
FIG. 11 illustrates enzyme purification as a function of the percentage evaporation.

The beneficial effect on the yield of enzyme by evaporating the fermentation broth is illustrated in FIG. 11. As evaporation is increased, the amount of enzyme isolated increased from 40% to a maximum of 90%. The amount of fermentation broth loaded on the column did not affect the yield of enzyme. The amount of enzyme isolated by this procedure was not limited by the capacity of the resin as the enzyme was recovered in the wash fractions and was not desorbed.

FIG. 11 illustrates that as the amount of fermentation broth increases the purification factor of isolated enzyme averaged over the fractions decreases. This reduction in purity of isolated enzyme and the concomitant increase in the amount of impurities in the wash fractions is due to the limited capacity of the resin to bind impurities. The maximum enrichment factor achieved as the amount of fermentation broth employed increased was about 2.6.

EXAMPLE 5

α-amylase produced by a species of thermophilic Archaebacteria was isolated using Fractogel EMD (M) TMAE according to the methodology described in Example 4. Although the fermentation medium employed contained approximately 0.5M NaCl, α-amylase was bound to the Fractogel and eluted with a resulting yield of 95%. The purification factor was improved when stepwise elution was employed. The average purification factor of the eluate fractions on desorption of the enzyme with a 1M NaCl solution was 1.25, whereas a considerably higher average purification factor of 5 was reached when the enzyme was eluted with a 0.2M NaCl solution.

What is claimed is:

1. A method for isolating an enzyme from a microbial cell-containing fermentation broth in which the enzyme is produced, comprising the steps of:
   (a) mixing in a container said broth with a particulate material capable of binding the enzyme, to form a mixture;
   (b) fluidizing the mixture resulting from step (a) by passing an ascending stream of inert gas through said mixture at a rate effective to mix the contents of said mixture in said container so that said enzyme in said broth binds to said particulate material, said stream of gas evaporating said mixture thereby increasing the concentration of said broth to enhance binding of said enzyme to the particulate material;
   (c) removing said broth from said mixture, leaving said enzyme bound to said particulate material; and
   (d) recovering bound enzyme from said particulate material by elution.

2. A method according to claim 1, wherein said enzyme is an α-amylase or alkaline protease.

3. A method according to claim 1, wherein said stream of gas is passed through said container until the enzyme loading of the particulate material is effective for maximum recovery of said enzyme from said suspension by said method.

4. A method according to claim 1, wherein said ascending stream of gas is heated.

5. A method according to claim 1, wherein said mixture is heated during evaporation.

6. A method according to claim 5, wherein said heat is accomplished by applying an external heat source to said container containing said mixture.

7. A method according to claim 1, wherein said steps (a) through (d) are carried out in a vertical container.

8. A method according to claim 7, wherein said vertical container is a column.

9. A method according to claim 1, wherein said gas is dry nitrogen.

10. A method according to claim 4, wherein said stream of gas is heated to enzyme-tolerable temperatures.

11. A method according to claim 5, wherein said stream of gas and said mixture are heated to enzyme-tolerable temperatures.

12. A method according to claim 1, wherein said particulate material is an ion exchange resin and wherein said resin is adjusted to a pH at which said enzyme is stable, said pH differing by at least one pH unit from the isoelectric point of said enzyme.

13. A method according to claim 12, wherein said particulate material has a particle size ranging from 50 to 1000 μm.

14. A method according to claim 12, wherein said particulate material has a particle size of about 100 μm.

15. A method according to claim 1, wherein said broth is removed from said container by a pulse of compressed gas.

16. A method according to claim 1, further comprising the steps of washing said enzyme bound to said particulate material from step d) prior to eluting said enzyme.

17. A method according to claim 1, wherein said broth is added to said container in aliquots and evaporation of said mixture is performed after the addition of each said aliquot.

18. A method according to claim 16, wherein said washing liquid is subsequently passed over a fixed bed column containing said particulate material.

19. A method according to claim 18, wherein said particulate material is ion exchange resin.

20. A method according to claim 1, wherein said eluting of said enzyme is carried out stepwise.

* * * * *